United States Patent
Nishio et al.

(10) Patent No.: US 8,309,345 B2
(45) Date of Patent: Nov. 13, 2012

(54) METHOD FOR DETECTING AN ANTIGEN

(75) Inventors: Kazuaki Nishio, Osaka (JP); Nozomu Matsukawa, Nara (JP); Shigeo Yoshii, Osaka (JP)

(73) Assignee: Panasonic Corporation, Osaka (JP)

(*) Notice: Subject to any disclaimer, the term of this patent is extended or adjusted under 35 U.S.C. 154(b) by 0 days.

(21) Appl. No.: 13/296,879

(22) Filed: Nov. 15, 2011

(65) Prior Publication Data

US 2012/0058490 A1 Mar. 8, 2012

Related U.S. Application Data

(63) Continuation of application No. PCT/JP2011/001989, filed on Apr. 1, 2011.

(30) Foreign Application Priority Data

Jun. 3, 2010 (JP) ................ 2010-127456

(51) Int. Cl.
*C12M 1/34* (2006.01)
*C12M 3/00* (2006.01)
(52) U.S. Cl. ............. 435/287.1; 435/7.9; 435/7.91; 435/283.1; 435/287.2
(58) Field of Classification Search ............. 435/7.1, 435/7.9, 7.91, 283.1, 287.1, 287.2
See application file for complete search history.

(56) References Cited

U.S. PATENT DOCUMENTS

| 2001/0053529 A1* | 12/2001 | Gindilis ............ 435/7.1 |
| 2005/0282237 A1 | 12/2005 | Ishimori |
| 2010/0040910 A1 | 2/2010 | Kajino et al. |

FOREIGN PATENT DOCUMENTS

| JP | 2005-351662 | 12/2005 |
| JP | 2008-064514 | 3/2008 |

OTHER PUBLICATIONS

Irina Pozdnyakova et al., Non-linear effects of macromolecular crowding on enzymatic activity of multi-copper oxidase, Biochimica et Biophysica Acta, Mar. 2, 2010, vol. 1804/No. 4, pp. 740-744.

* cited by examiner

*Primary Examiner* — Melanie J Yu
(74) *Attorney, Agent, or Firm* — McDermott Will & Emery LLP

(57) ABSTRACT

Provided is a method for detecting an antigen without use of a labeled-antibody. A support having an antibody and a multi-copper oxidase CueO immobilized thereon is brought into contact with a first buffer solution containing the antigen, a current is measured by a potentiostat method using the support and a second buffer solution, and when the measured current is greater than or equal to 1.5×(blank value), it is determined that the antigen exists. The second buffer solution contains a substrate of the CueO and has an ionic strength falling within a range of not less than 0.3 mM and not more than 1.0 mM.

9 Claims, 5 Drawing Sheets

METHOD FOR DETECTING AN ANTIGEN

CROSS-REFERENCE TO RELATED APPLICATIONS

This is a continuation of PCT International Application No. PCT/JP2011/001989, filed on Apr. 1, 2011, claiming priority of Japanese Patent Application No. 2010-127456, filed on Jun. 3, 2010, the disclosures of which Applications are hereby incorporated by reference.

BACKGROUND OF THE INVENTION

1. Field of the Invention

The present invention relates to a method for detecting an antigen with use of an antibody and an enzyme.

2. Description of the Background Art

Patent Literature 1 discloses an enzyme immunoassay method. FIG. 2 shows a sandwich method, which is included in the enzyme immunoassay method.

As shown in FIG. 2, a support 107 has an antibody 108 on its surface. The sample containing an antigen 109 is supplied to the surface of the support to cause the antigen 109 to be bound specifically to the antibody 108. Subsequently, the sample containing the unreacted antigen 109 was removed by washing.

Next, a labeled-antibody 111 comprising an enzyme 110 which detects the antigen 109 is supplied to the surface of the support 107 to form the complex composed of the antibody 108, the antigen 109, and the labeled-antibody 111. Subsequently, the sample containing the unreacted labeled-antibody 111 was removed by washing.

Finally, a substrate 112 of the enzyme 110 is supplied to the surface of the support 107. The enzyme 110 reacts with the substrate 112 metabolically to form a product 113. The luminescence degree or light absorption degree of the product 113 is measured to detect the antigen 109 indirectly.

However, the sandwich method requires not only the antigen 108 but also the labeled-antibody 111 comprising the enzyme 110. It is necessary that the labeled-antibody 111 is supplied after the specific reaction between the antibody 108 and the antigen 109. Furthermore, the unreacted labeled-antibody 111 is required to be removed.

CITATION LIST

Patent Literature

[Patent Literature 1] Japanese Patent Publication No. 4271086

SUMMARY OF THE INVENTION

Technical Problem

The purpose of the present invention is to provide a method for detecting an antigen without use of a labeled-antibody.

Solution to Problem

1. A method for detecting an antigen, the method comprising steps of:

a step (A) of bringing a support into contact with a first buffer solution to be predicted to contain the antigen, wherein
an antibody and a multi-copper oxidase CueO are immobilized on the support,
the support is electrically conductive,
the antibody reacts specifically to the antigen,
a step (B) of measuring a current by a potentiostat method using the support and a second buffer solution,
wherein the second buffer solution contains a substrate of the multi-copper oxidase CueO,
the second buffer solution has an ionic strength falling within a range of not less than 0.3 mM and not more than 1.0 mM, and
a step (C) of determining that the antigen exists in the first buffer solution if the following inequality is satisfied:
the current measured in the step (B)$>=1.5\times$(blank value)
wherein the blank value is a current measured with a potentiostat method in which the antigen is not used but the second buffer solution is used.

2. The method according to item 1, wherein the support is composed of carbon.

3. The method according to item 1, wherein the second buffer solution has a pH of not less than 5.0 and not more than 6.0.

4. The method according to item 1, wherein the second buffer solution contains oxygen and proton.

5. The method according to item 1, wherein the first buffer solution is a Tris-buffered HCl solution, a Tris-buffered saline, or a phosphate buffer saline.

6. The method according to item 1, wherein the second buffer solution is an acetic acid buffer solution, a citrate buffer solution, a succinic acid buffer solution, a phthalic acid solution, or a 2-morpholinoethanesulfonic acid.

7. The method according to item 5, wherein the second buffer solution is an acetic acid buffer solution, a citrate buffer solution, a succinic acid buffer solution, a phthalic acid solution, or a 2-morpholinoethanesulfonic acid.

Advantageous Effect of Invention

The present invention provides a method for detecting an antigen without use of a labeled-antibody.

DESCRIPTION OF THE PREFERRED EMBODIMENTS

The embodiment of the present invention is described below with reference to the drawings.

Figure 1:
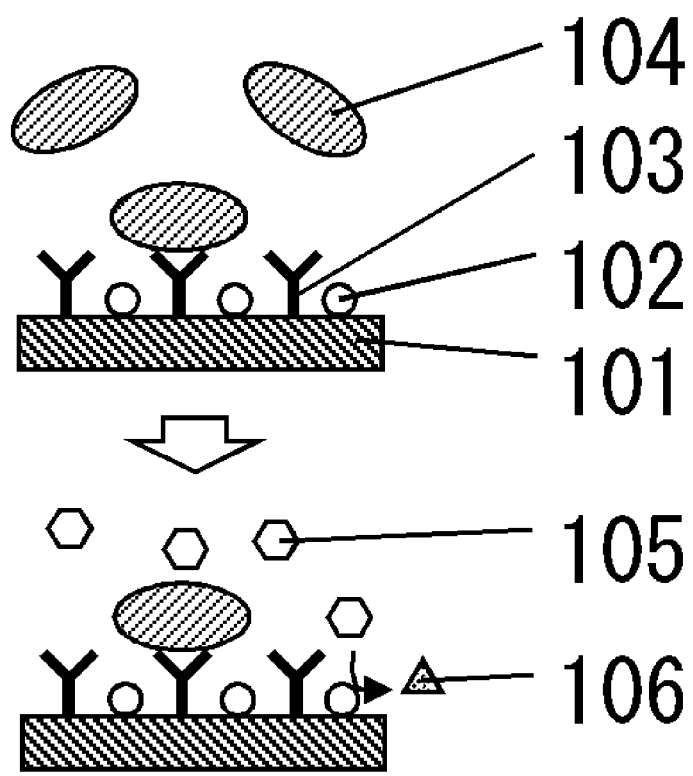
FIG. 1 shows a reaction flowchart of the method for detecting an antigen according to the present invention.
Figure 2:
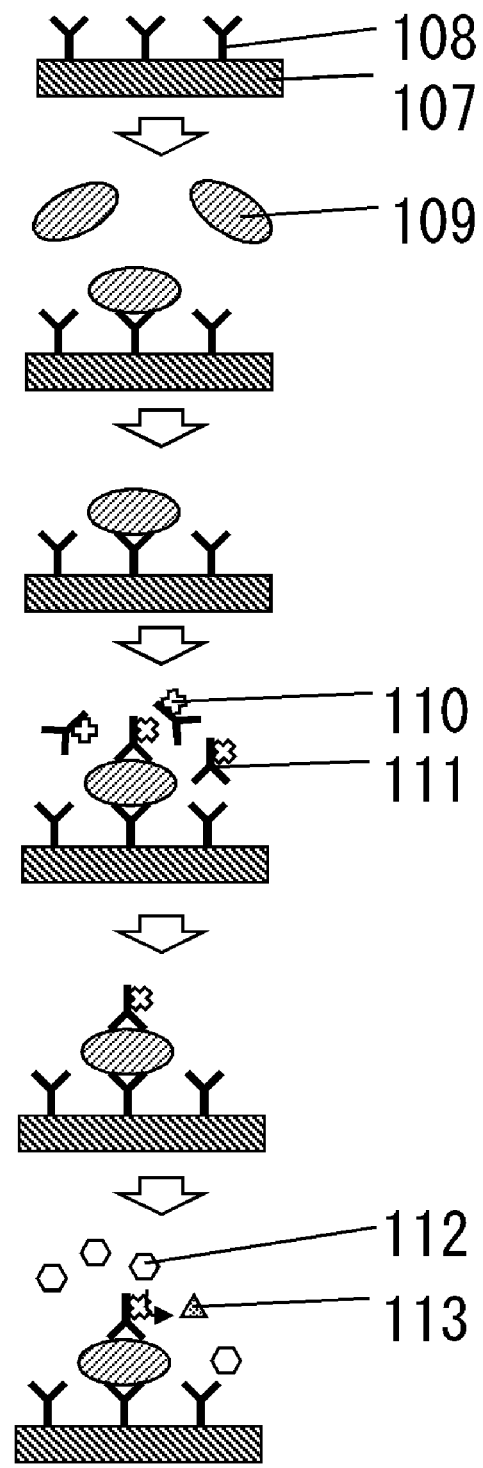
FIG. 2 shows a reaction flowchart of the conventional enzyme immunoassay method (sandwich method).

FIG. 1 shows a reaction flowchart of the method for detecting an antigen according to the present invention.

(Step (A))

In the step (A), a support 101 is brought into contact with a first buffer solution 101 which is predicted to contain an antigen 104.

An example of the antigen 104 detected by the present invention is a virus, a *bacillus*, a fungus, a protein, or an oligonucleotide. A virus, a *bacillus*, or a fungus is preferred.

An example of the first buffer solution is a Tris-buffered HCl solution, a Tris-buffered saline, or a phosphate buffer saline. Preferably, the first buffer solution has near-neutral pH.

The support 101 comprises a multi-copper oxidase 102 and an antibody 103 on its surface.

The support 101 is required to be electrically conductive, since the support 101 forms part of a working electrode in the step (B). A preferred example of the material of the support 101 is carbon. As the carbon, carbon nanotube, carbon black, ketjen black, glassy carbon, or a highly-oriented pyrolytic graphite (HOPG) are preferably used. Carbon nanotube is more preferred.

As shown in FIG. 1, the antibody 103 and multi-copper oxidase 102 are immobilized on the surface of the support 101. The antibody 103 reacts specifically with the antigen 104.

The antibody 103 may be a polyclonal antibody or a monoclonal antibody. A Fab fragment antibody and F(ab')2 fragments antibody, in which its Fc region is removed artificially, may be used.

The multi-copper oxidase 102 is one enzyme which catalyzes an oxidation-reduction reaction. In the present specification, the multi-copper oxidase 102 may be represented as "CueO". The multi-copper oxidase 102 performs four-electron reduction of the substrate 105 composed of molecular oxygen and catalyzes the reaction in which water is formed as a product 106. The active center of the multi-copper oxidase 102 is consisted of four copper ions having differential property called type 1, type 2, type 3a, and type 3b.

The preferred multi-copper oxidase 102 is laccase. It is more preferred that the CueO derived from *Escherichia coli* is used.

The method for immobilizing the antibody 103 and the multi-copper oxidase 102 on the support 101 includes the following methods (a) and (b):

Method (a): a method using non-specific absorption due to hydrophobic interaction between the antibody 103 and the multi-copper oxidase 102, and Method (b): a method for chemically binding the support 101 to the antibody 103 or the multi-copper oxidase 102.

A concrete method (b) is described below.

Carboxyl group is introduced to the support 101. The carboxyl group is treated with 1-ethyl-3-(3-dimethylaminopropyl)-carbodiimide and N-hydroxysuccineimide. Subsequently, the antibody 103 and the multi-copper oxidase 102 are added. The amino group in the lysine residue which the surface of the antibody 103 has reacts with the carboxyl group to form the amido bond. Similarly, the amino group in the lysine residue which the surface of the multi-copper oxidase 102 has also reacts with the carboxyl group to form the amido bond.

The method for bringing the support 101 into contact with the first buffer solution includes the following methods:

Method (I): a method for coating the surface of the support 101 with the first buffer solution, and Method (II): a method for immersing the support 101 in the first buffer solution.

The contact causes the specific binding of the antibody 103 to the antigen 104. Subsequently, the first buffer solution containing the unreacted antigen 104 was removed from the surface of the support 101.

In the present invention, the specific binding of the antibody 103 to the antigen 104 increases of the enzyme activity of the multi-copper oxidase 102.

(Step (B))

In the step (B), a current is measured by a potentiostat method with use of the support 101 and a second buffer solution.

The second buffer solution contains a substrate 105 of the multi-copper oxide CueO. Examples of the substrate 105 are oxygen and proton. These are contained in an ordinal and commercially-available buffer solution.

It is preferred that the second buffer solution has pH of not less than 5.0 and not more than 6.0. Sodium hydroxide, potassium hydroxide, ammonia, and trimethylammonium are used to adjust the pH. An example of the second buffer solution is an acetic acid buffer solution, a citrate buffer solution, a succinic acid buffer solution, a phthalic acid solution, or MES (2-morpholinoethanesulfonic acid). An acetic acid buffer solution is preferred.

The second buffer solution is required to have an ionic strength falling within a range of not less than 0.3 mM and not more than 1.0 mM. When the ionic strength is less than 0.3 mM, it is difficult to ensure the stability of the pH. When the ionic strength is more than 1.0 mM, as is clear from the examples described later, it is difficult to detect the antibody contained in the first buffer solution.

Figure 3:
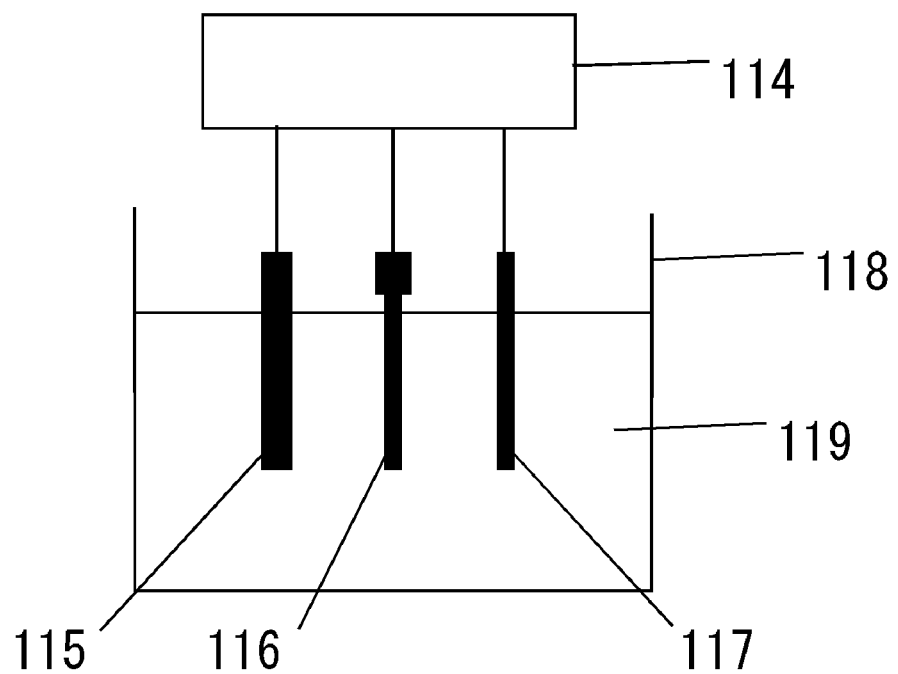
FIG. 3 shows a fundamental structure of the electrochemical measurement device used in the method for detecting an antigen according to the present invention.

FIG. 3 shows an electrochemical measurement device used for a potentiostat method. The electrochemical measurement device comprises a meter 114 composed of a potentiostat, a working electrode 115, a reference electrode 116, and a counter electrode 117.

An example of the reference electrode 116 is a saturated KCl silver/silver chloride electrode. An example of the counter electrode 117 is a Pt electrode. The working electrode 115 comprises the support 101.

Figure 5:
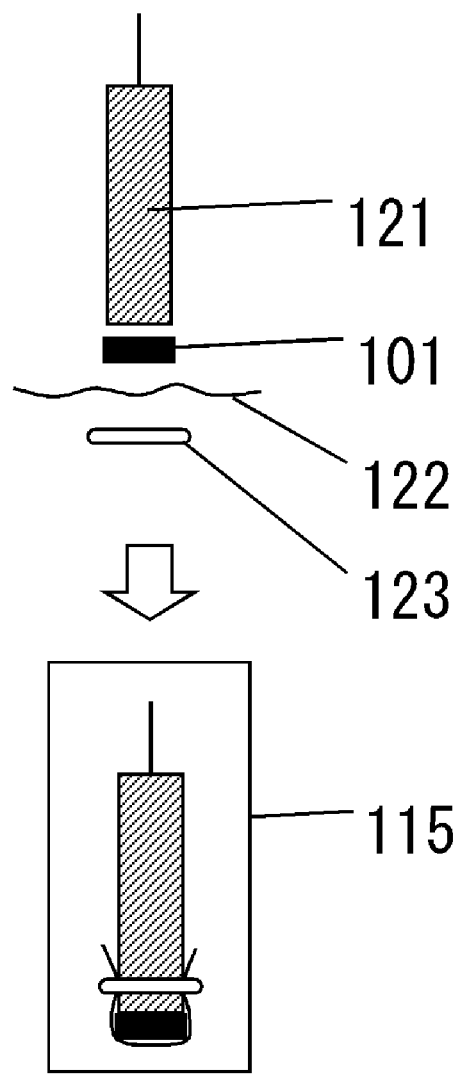
FIG. 5 shows an example of the electrochemical measurement in the example 1.

FIG. 5 shows an example of the working electrode 115. The working electrode 115 comprises the support 101 fixed at the end of a glassy carbon electrode 121. The end of a glassy carbon electrode 121 further comprises a net 122 and a ring 123. The support 101 is fixed at the end of the glassy carbon electrode 121 by the net 122 and the ring 123. Preferably, the material of the net 122 is nylon.

As shown in FIG. 3, these three electrodes 115-117 connected to the meter 114 are immersed in a second buffer solution 119 stored in a reaction tank 118. Subsequently, a current is measured by the potentiostat method. In the potentiostat method, a sweep may be performed between an initial potential of 0.6 volts and a terminal potential of 0 volts. A reduction current caused by the enzyme activity of the multi-copper oxidase 102 is increased when the potential comes closer to 0 volts. As is clear from the example 1 described later, the current is varied little during the period between the initial potential of 0.6 volts and the potential of 0.45 volts. This is because the reaction of the multi-copper oxidase 102 proceeds little during this period.

Figure 4:
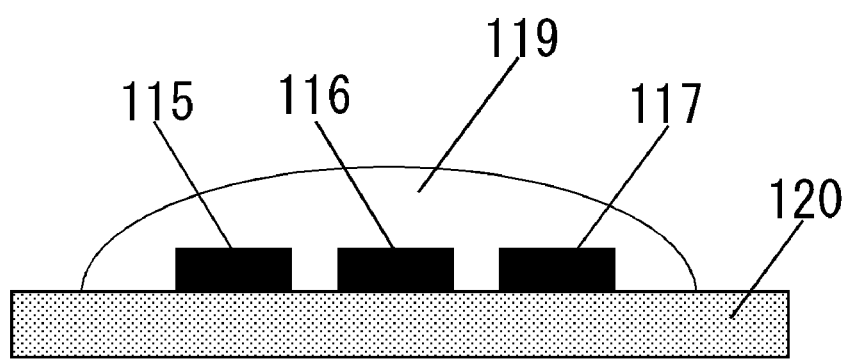
FIG. 4 shows a fundamental structure of the working electrode used in the method for detecting an antigen according to the present invention.

Instead of immersing the three electrodes 115-117 in the second buffer solution 119, as shown in FIG. 4, the second buffer solution 119 may cover the working electrode 115, the reference electrode 116, and the counter electrode 117. The three electrodes 115-117 shown in FIG. 4 are disposed on the surface of the substrate 120.

(Step (C))

In the step (C), if the following inequality is satisfied, it is determined that the first buffer solution contains the antigen:

(the current measured in the step (B))≧1.5×(blank value).

Here, the blank value is a current measured by the potentiostat method where the antigen is not used, however, the second buffer solution is used.

The antigen is detected by the determination.

The blank value is calculated in parallel with the step (C). Alternatively, the blank value is calculated beforehand.

The present invention is described in more detail by the following example 1.

Example 1

Preparation of Antibody

A solution containing an anti-Bovine Serum Albumin antigen (anti-BSA antigen: IgG fraction of anti-Albumin (Bovine Serum) [Rabbit]; available from Rockland Immunochemicals, Inc.) was used. The solvent of the solution was substituted with 10 mM tris(hydroxylmethyl)aminomethane-hydrochloric acid buffer solution (Tris-hydrochloric acid buffer solution) (pH: 7.5) with use of an ultrafiltration unit (Amicon Ultra-4.MWCO: 30,000; available from Millipore Corp.).

After the solvent was substituted, the concentration of the antigen was measured on the basis of Bradford method (Protein assay kit II; available from Bio-Rad Laboratories, Inc.) with use of Bovine Serum Albumin (BSA) as a standard. The antibody has a concentration of 20 mg/mL. The obtained anti-BSA antibody was stored at 4 degrees Celsius.

(Preparation of a CueO solution)

As described below, a CueO derived from *Escherichia coli* (K-12) was produced in the *Escherichia coli* as a recombinant CueO and the CueO was purified.

The gene of the CueO was amplified by a PCR method using *Escherichia coli* genomic DNA (LA genome DNA set for PCR, available from Takara Bio Inc.).

In the PCR, a base sequence coding for histidine tag was added to an oligo DNA primer and the histidine tags were added to the carboxyl terminal side of the amino acid sequence of the CueO.

The amplified DNA fragment was cloned (In-Fusion Dry-Down PCR Cloning Kits; available from Clontech laboratories, Inc.) to an expression vector (pRSFDuet-1, available from Merck KGaA). With use of the expression vector, *Escherichia coli* (BL21(DE3); available from Agilent Technologies, Inc.) was transformed. The transformed *Escherichia coli* were incubated for sixteen hours on a LB broth containing copper sulfate with a concentration of 1 mM.

A periplasm fraction was extracted from the recovered fungus body, and CueO was purified from the extraction liquid with use of a histidine tag purification column (TALON CellThru Resin; available from Clontech laboratories, Inc.) and an anion-exchange column (HiTrap Q HP 5 mL; available from GE Healthcare).

With use of a desalination column (HiTrap desalting; available from GE Healthcare), the solvent of the solution containing the purified CueO was substituted with 10 mM of tris-hydrochloric acid buffer solution (pH: 7.5). Subsequently, the CueO solution was condensed with use of the ultrafiltration unit (Amicon Ultra-4, MWCO: 30,000; available from Millipore Corp.). The condensed CueO solution has a concentration of 4 mg/mL. The concentration of the CueO solution was measured by the Bradford method using BSA as a standard. The obtained CueO solution was stored at four degrees Celsius.

(Preparation of Support)

Dimethylsulfoxide (DMSO) with a volume of 5 mL was added to 5 mg of carbon nanotube (SWCNT; available from Sigma-Aldrich Corp.). Subsequently, the DMSO solution was homogenized for three minutes with use of an ultrasonic homogenizer (sonifier 150; available from Branson Ultrasonics Corp.) at an output of 10 watts (RMS) to obtain a SWCNT suspension.

A carbon felt with a diameter of 6 millimeters was cut from a carbon felt (available from Nippon Carbon Co., Ltd) with a thickness of 2 millimeters. The carbon felt was fixed to a column made of plastic (Bio spin empty column; available from Bio-Rad Laboratories, Inc.).

The SWCNT suspension with a volume of 500 microliters was dripped onto the carbon felt so as to allow it to absorb the carbon nanotube. DMSO with a volume of 0.3 mL and ultra-pure water with a volume of 3 mL were flowed through the column in this order. Next, 1 mL of tris-hydrochloride buffer solution (pH: 7.5, 10 mM) was flowed through the column, and the column was washed. The carbon felt obtained in the column was used as the support.

(Immobilization of the CueO Solution and the Antibody to the Support)

The tris-hydrochloride buffer solution (pH: 7.5, 10 mM) with a volume of 0.1 mL containing the CueO solution with a concentration of 2 mg/mL and the anti-BSA antibody with a concentration of 6 mg/mL was dripped onto to the column where the above-mentioned support was set. Incubation at a temperature of 25 degrees Celsius for ten minutes caused the CueO and the anti-BSA antibody to be bonded to the support composed of the carbon felt. In this manner, the CueO and anti-BSA antibody were immobilized.

An ice-chilled tris-hydrochloride buffer solution (pH: 7.5, 10 mM) with a volume of 2 mL was flowed through the column. The obtained support was stored at a temperature of four degrees Celsius.

(Preparation of an Acetic Acid Buffer Solution)

While pH was measured with use of a pH meter, sodium hydroxide was added to acetic acid to prepare an acetic acid buffer solution with a concentration of 1M and with a pH of 3. The acetic acid buffer solution was diluted by 0.1% to prepare an acetic acid buffer solution with a concentration of 1.0 mM (pH: 3). Similarly, an acetic acid buffer solution with a concentration of 1M and with a pH of 6 was prepared. Furthermore, an acetic acid buffer solution with a concentration of 1 mM and with a pH of 6 was prepared.

While pH was measured with use of an pH meter, the acetic acid buffer solution (pH: 3) with a concentration of 1.0 mM was added to the acetic acid buffer solution (pH: 6) with a concentration of 1.0 mM to prepare the acetic acid buffer solution (pH: 5.5) with a concentration of 1.0 mM. During the pH adjustment, the temperature was 25 degrees Celsius.

Similarly, acetic acid buffer solutions each having a concentration of 0.5 mM, 5 mM, and 10 mM were prepared.

(Electrochemical Measurement by a Potentiostat Method)

The enzyme activity of the CueO was measured by an electrochemical measurement with use of a potentiostat method. The electrochemical measurement device shown in FIG. 3 was used. The meter 114 was a potentiostat (ALS760C, available from BAS Inc.). The reference electrode 116 was a saturated KCl silver/silver chloride electrode (RE-1C, available from BAS Inc.). The counter electrode 117 was a Pt electrode (length: 23 centimeters, available from BAS Inc.).

As shown in FIG. 1 and FIG. 5, the support 101 comprising the antibody 103 and the multi-copper oxidase 102 was fixed to the glassy carbon electrode 121 (Electrode side (ID): 3 mm, available from BAS Inc.) by the nylon net 121 and the ring 123 to obtain the working electrode 115.

(Calculation of the Blank Value)

The measurement was performed with use of the working electrode 115. An acetic acid buffer solution (pH: 5.5, 1 mM) with a volume of 10 mL was supplied to a cell as a supporting electrolyte. The working electrode 115, the reference electrode 116, and the counter electrode 117 were immersed in the cell. The immersion caused the tris-hydrochloride buffer solution (pH: 7.5) with a concentration of 10 mM to be substituted with the acetic acid buffer solution with a concentration of 1 mM.

By the potentiostat method at a temperature of 25 degrees Celsius, a sweep was performed at a sweep speed of 20 mM/sec between the initial potential of 0.6 volts and the terminal potential of 0 volts, and the current value was measured. Referential sign (2) in FIG. 6 indicates the measurement result.

A reduction current caused by the enzyme activity of the CueO was increased when the potential went from 0.6 volts closer to 0 volts. Since the enzyme reaction proceeded little during the period between the initial potential of 0.6 volts and the potential of 0.45 volts, the current value at the potential of 0.45 volts was defined as a standard value (Referential sign "(1)" in FIG. 6). The blank value was defined by the following equation:

(The blank value)=(The current value (2) measured)−
(The standard value (1))

(Detection of the Antigen)

The support where the CueO and the antibody were immobilized was fixed to one end of a column made of plastic. A tris-hydrochloride buffer solution (pH: 7.5, 10 mM) with a concentration of 1 mL was flowed through the column.

Next, a tris-hydrochloride buffer solution (25 mg/mL, pH: 7.5, 10 mM) with a volume of 1 mL containing silica beads (300 nanometers, available from micromod Partikeltechnologie GmbH) was flown to the column. Each of the silica beads was coated with BSA, which is the antigen.

The solution flown from the end of the column was recovered, and the solution was flowed through the column again. This was repeated ten times. Finally, a tris-hydrochloride buffer solution (10 mM, pH: 7.5) with a volume of 2 mL was flowed through the column.

The support was removed from the column. As shown in FIG. 5, the support 101 was fixed to the end of the glassy carbon electrode 121 with the nylon net 122 and the ring 123 to obtain the working electrode 115.

Figure 6:
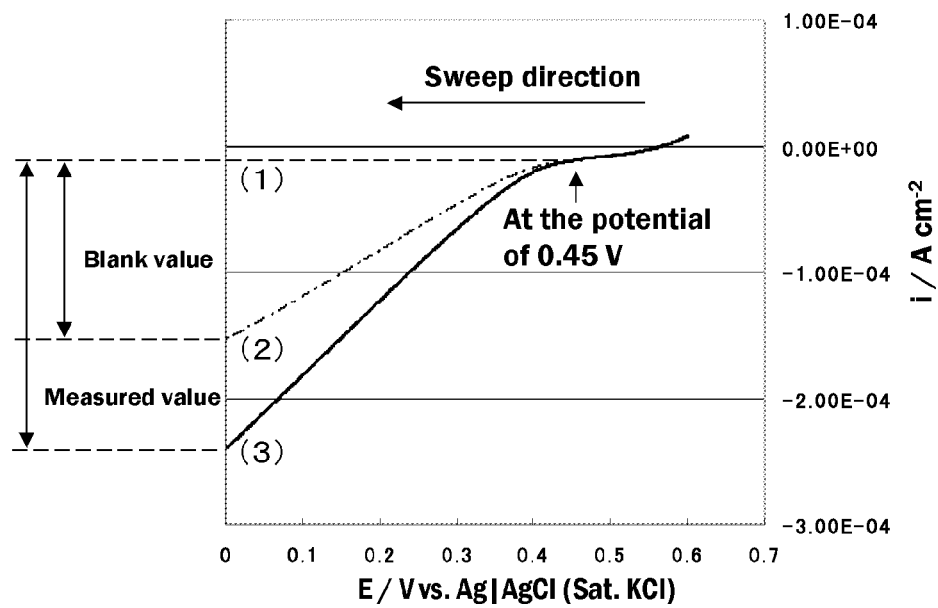
FIG. 6 is a graph showing the results of the electrochemical measurement in the example 1.

Similarly to the measurement of the blank value, the working electrode 115 was immersed into the cell containing the acetic buffer solution (pH: 5.5, 1.0 mM) with a volume of 10 mL. By the potentiostat method at a temperature of 25 degrees Celsius, a sweep was performed at a sweep speed of 20 mV/sec between the initial potential of 0.6 volts and the terminal potential of 0 volts, and the current value was measured. Referential sign (3) in FIG. 6 shows the measurement result.

The measurement value was defined by the following equation:

(The measurement value)=(The current value (3) measured)−(The standard value (1)).

An amplification ratio was defined in the following equation:

(The amplification ratio)=(the measurement value)/
(the blank value).

With use of acetic buffer solutions (pH: 5.5) each having a concentration of 0.5 mM, 5 mM, and 10 mM, the amplification ratios were obtained similarly to the above-mentioned case.

Table 1 shows the blank values, the measurement values, and the amplification ratios when the sweep potential is 0.0 volts, 0.1 volts, 0.2 volts, and 0.3 volts.

TABLE 1

| Concentration of Acetic Acid Buffer Solution (mM) | Potential (V) | Blank Value [A] (A/cm$^2$) | Measurement Value [B] (A/cm$^2$) | Amplification ratio [B/A] |
|---|---|---|---|---|
| 0.5 | 0.0 | −5.5.E−05 | −1.2.E−04 | 2.21 |
|  | 0.1 | −4.2.E−05 | −9.1.E−05 | 2.17 |
|  | 0.2 | −2.8.E−05 | −5.9.E−05 | 2.14 |
|  | 0.3 | −1.4.E−05 | −2.9.E−05 | 2.12 |
| 1 | 0.0 | −1.4.E−04 | −2.3.E−04 | 1.61 |
|  | 0.1 | −1.1.E−04 | −1.7.E−04 | 1.58 |
|  | 0.2 | −7.1.E−05 | −1.1.E−04 | 1.55 |
|  | 0.3 | −3.5.E−05 | −5.4.E−05 | 1.54 |
| 5 | 0.0 | −3.6.E−04 | −4.1.E−04 | 1.14 |
|  | 0.1 | −2.8.E−04 | −3.2.E−04 | 1.14 |
|  | 0.2 | −1.8.E−04 | −2.1.E−04 | 1.14 |
|  | 0.3 | −8.9.E−05 | −1.0.E−04 | 1.14 |
| 10 | 0.0 | −5.1.E−04 | −5.4.E−04 | 1.07 |
|  | 0.1 | −4.0.E−04 | −4.2.E−04 | 1.07 |
|  | 0.2 | −2.6.E−04 | −2.8.E−04 | 1.07 |
|  | 0.3 | −1.3.E−04 | −1.4.E−04 | 1.07 |

As understood from Table 1, when the concentration of the acetic acid buffer solution was 0.5 mM or 1.0 mM, the amplification ratio of not less than 1.5 was obtained. On the contrary, when the concentration of the acetic acid buffer solution was not less than 5 mM, the amplification ratio was small.

Accordingly, when the amplification ratio, which was measured by the potentiostat method with use of the second buffer solution with a concentration of not more than 1.0 mM, is not less than 1.5, a skilled person would understand from Table 1 that the first buffer solution contains the antigen. Thus, the antigen is detected in the present invention. Furthermore, a skilled person would understand easily that the labeled-antibody 111 is not used in the present invention.

INDUSTRIAL APPLICABILITY

The present invention is used for a biosensor. The present invention is very useful for quick immunodiagnosis with multiplex assay.

REFERENCE SIGNS LIST

| | |
|---|---|
| 101: | support |
| 102: | multi-copper oxidase |
| 103: | antibody |
| 104: | antigen |
| 105: | substrate |
| 106: | product |
| 107: | support |
| 108: | antibody |
| 109: | antigen |
| 110: | enzyme |
| 111: | labeled-antibody |
| 112: | substrate |
| 113: | product |
| 114: | meter |
| 115: | working electrode |
| 116: | reference electrode |

| | |
|---|---|
| 117: | counter electrode |
| 118: | reaction tank |
| 119: | buffer solution with a low ionic intensity |
| 121: | glassy carbon electrode |
| 122: | nylon net |
| 123: | ring |

What is claimed is:

1. A method for detecting an antigen using an electrochemical measurement device comprising a working electrode, a reference electrode, and a counter electrode, the method comprising steps of:
(A) contacting an electrically conductive support with a sample solution, the support including a mixture of an antibody specifically reacting with the antigen and a multi-copper oxidase CueO;
(B) measuring a current between the working electrode and the counter electrode by way of a potentiostat method, the potentiostat method comprising the steps of:
(i) equipping the contacted support with the working electrode; and
(ii) contacting the working electrode, the reference electrode, and the counter electrode with a buffer solution, the buffer solution having an ionic strength falling within a range of not less than 0.3 mM and not more than 1.0 mM, and containing a substrate of the multi-copper oxidase CueO; and
(C) determining that the antigen is contained in the sample solution if the following inequality is satisfied:
the current measured in the step >=1.5×(blank value)
where the blank value is a current between the working electrode and the counter electrode measured by way of the potentiostat method under the condition that the antigen is not contained in the sample solution.

2. The method according to claim 1, wherein the support is formed of carbon.

3. The method according to claim 1, wherein the buffer solution has a pH of not less than 5.0 and not more than 6.0.

4. The method according to claim 1, wherein the second buffer solution contains oxygen and proton.

5. The method according to claim 1, wherein the sample solution is a Tris-buffered HCl solution, a Tris-buffered saline, or a phosphate buffer saline.

6. The method according to claim 1, wherein the buffer solution is an acetic acid buffer solution, a citrate buffer solution, a succinic acid buffer solution, a phthalic acid solution, or a 2-morpholinoethanesulfonic acid buffer solution.

7. The method according to claim 5, wherein the buffer solution is an acetic acid buffer solution, a citrate buffer solution, a succinic acid buffer solution, a phthalic acid buffer solution, or a 2-morpholinoethanesulfonic acid buffer solution.

8. The method according to claim 1, wherein the antigen is an anti-Bovine Serum Albumin.

9. The method according to claim 8, wherein the buffer solution is an acetic buffer solution.

* * * * *